US006492116B1

(12) United States Patent
Chène et al.

(10) Patent No.: US 6,492,116 B1
(45) Date of Patent: Dec. 10, 2002

(54) ASSAY FOR IDENTIFYING INHIBITORS OF THE INTERACTION BETWEEN PROTEINS P53 AND DM2

(75) Inventors: Patrick Chène, Mulhouse (FR); Heinz-Kurt Hochkeppel, Aesch (CH)

(73) Assignee: Cancer Research Campain Technology Ltd. (GB)

( * ) Notice: Subject to any disclaimer, the term of this patent is extended or adjusted under 35 U.S.C. 154(b) by 0 days.

(21) Appl. No.: 09/603,052

(22) Filed: Jun. 26, 2000

Related U.S. Application Data

(63) Continuation of application No. 09/029,440, filed as application No. PCT/EP96/03957 on Sep. 10, 1996, now abandoned.

(30) Foreign Application Priority Data

Sep. 18, 1995 (EP) ............................................. 95810576
Sep. 18, 1995 (EP) ............................................. 95810576

(51) Int. Cl.[7] .......................... C12Q 1/68; C12P 19/34; C07M 21/02
(52) U.S. Cl. ......................... 435/6; 435/91.2; 536/23.1; 536/24.3; 436/501
(58) Field of Search ................... 435/6, 91.2; 536/23.1, 536/24.3; 436/501

(56) References Cited

U.S. PATENT DOCUMENTS 5,770,377 A * 6/1998 Picksley et al. ............. 435/7.1

FOREIGN PATENT DOCUMENTS

| EP | 0518650 | 12/1992 |
| WO | 9320238 | 10/1993 |

OTHER PUBLICATIONS

Zauberman et al, "Sequence specific DNA binding by p53: identification of target sites and lack of binding to p53–MDM2 complexes", EMBO J. 12(7):2799–2808, 1993.*

Brown et al, "The tumor suppressor p53 and the oncoprotein simian virus 40 T antigen bind to overlapping domains on the mdm2 protin", Mol. Cell Biol. 13(11):6849–6857, Nov. 1993.*

Marston et al, "Oligomerisation of full length p53 contributes to the interaction with mdm2 but not hpv E6", Oncogene 10:1709–1715, 1995.*

Stratagene Catalog, p. 39, 1988.*

Alder H. et al., "A conserved region in intron 1 negatively regulates the expression of the PCNA gene", Proc. Annu. Meet. Am. Assoc. Cancer Res. , vol. 33, 1992, A:2163.

Arroyo M et al., "Retinoblastoma–repression of E2F–dependent transcription depends on the ability of the retinoblastoma protein to interact with E2F and is abrogated by the adenovirus E1A oncoprotein" Nucleic Acids Research, vol. 20, No. 22, 1992 pp. 5947.

Badiali, M. et al., "p53 Gene Mutations in Medulloblastoma", Diagnostic Molecular Pathology, vol. 2, 1993, pp. 23–28.

Baker, A. et al., "A C–Terminal FMS Mutation in a Patient with B–Cell Malignancy", Leukemia, vol. 9, 1995, pp. 155–158.

Banks, L. et al., "Identification of Human Papillomavirus Type 18 E6 Polypeptide in Cells Derived from Human Cervical Carcinomas", J. Gen. Virol., vol. 68, 1987, pp. 1351–1359.

Beenken, S. et al., "An intron binding protein is required for transformation ability of p53", Nucleic Acids Research, vol. 19, 1991, pp. 4747–4752.

Bocco, J. et al., "Rb may act as a transcriptional co–activator in undifferentiated F9 cells", Oncogene, vol. 8, 1993, pp. 2977–2986.

Carder, P. et al., "Mutation of the p53 gene precedes aneuploid clonal divergence in colorectal carcinoma", British Journal of Cancer, vol. 71, 1995, pp. 215–218.

Carrier, F. et al., "Characterization and Nuclear Localization of Gadd45, a p53–Regulated Protein", Proc Annu. Meet. Am. Assoc. Cancer Res., vol. 35, 1994.

Chen, C. et al., "Interactions between p53 and MDM2 in a Mammalian Cell Cycle Checkpoint Pathway", Proc. Natl. Acad. Sci., vol. 91, 1994, pp. 2684–2688.

Chiou, C–J. et al., "Identification and Mapping of Dimerization and DNA–Binding Domains in the C Terminus of the IE2 Regulatory Protein of Human Cytomegalovirus", Journal of Virology, vol. 67, 1993, pp. 6201–6214.

Chittenden, T. et al., "Cell Cycle Analysis of E2F in Primary Human T Cells Reveals Novel E2F Complexes and Biochemically Distinct Forms of Free E2F", Molecular and Cellular Biology, vol. 134, 1993, pp. 3975–3983.

Choo, K.–B. et al., "Absence of Mutation in the p53 and the Retinoblastoma Susceptibility Genes in Primary Cervical Carcinomas", Virology, vol. 193, 1993, pp. 1042–1046.

Chumakov, A. et al., "Analysis of p53 Transactivation Through High–Affinity Binding Sites", Oncogene, vol. 8, 1993, pp. 3005–3011.

Coutinho, A., Memorias do Instituto do Oswaldo Cruz, Foreword, vol. 87, 1992, S4.

(List continued on next page.)

*Primary Examiner*—Jeffrey Fredman
(74) *Attorney, Agent, or Firm*—Knobbe, Martens, Olson & Bear, LLP

(57) ABSTRACT

The present invention concerns a new assay which allows the identification of compounds which inhibit the formation of complexes between a product of the double minute 2 gene ("dm2") and p53 but not between p53 and DNA. Both the complex formation of labeled DNA, C-terminally truncated p53 and dm2 and disruption of dm2 from the labeled DNA-p53 complex by an inhibitor of the p53-dm2 interaction can be detected by a gel shift assay procedure. This assay permits the selection of compounds which, besides their inhibitory property, do not alter p53 specific DNA binding and do not disturb p53 conformation required for DNA binding or formation of active tetramer.

9 Claims, No Drawings

OTHER PUBLICATIONS

Domann, F. E. et al., "Constitutive AP–1 DNA Binding and Transactivating Ability of Malignant but Not Benign Mouse Epidermal Cells", Molecular Carcinogenesis, vol. 9, 1994, pp. 61–66.

Drummond, I. A., "Repression of the Insulin–Like Growth Factor II Gene by the Wilms Tumor Suppressor WT1", Science, vol. 257, 1992, pp. 674–675.

Fakharzadeh, S. et al., "Tumorigenic Potential Associated with Enhanced Expression of a Gene that is Amplified in a Mouse Tumor Cell Line", The EMBO Journal, vol. 10, 1991, pp. 1565–1569.

Gauthier, J.–M., et al., "Structural analysis of the human papillomavirus type 16–E2 transactivator with antipeptide antibodies reveals a high mobility region linking the transactivation and the DNA–binding domains", Nucleic Acids Research, vol. 19, 1991, pp. 7073–7059.

Gong, Z., et al., "Zinc and DNA Binding Properties of a Novel LIM Homeodomain Protein Isl-2", Biochemistry, vol. 33, 1994, pp. 15149–15158.

Harada, H. et al., "Anti–Oncogenic and Oncogenic Potentials of Interferon Regulatory Factors–1 and –2", Science, vol. 259, 1993, pp. 971–974.

Hudson, J.M., et al., "Wild–type p53 downregulates its own transcription.", Proc. Annu. Meet. Am. Assoc. for Cancer Res., vol. 35, 1994, p. 604.

Huibregtse, J. M. et al., "Cloning and Expression of the cDNA for E6–AP, a Protein that Mediates the Interaction of the Human Papillomavirus E6 Oncoprotein with p53", Molecular and Cellular Biology, 1993, pp. 775–784.

Imai, Y. et al., "T antigen of SV40 blocks p53 transactivation but not p53 specific binding to DNA", International Journal of Oncology, vol. 5, 1994, pp. 945–953.

Jiang, D. et al., "SV40 T antigen abrogates p53–mediated transcriptional activity", Oncogene, vol. 8, 1993, pp. 2805–2812.

Kim, J.–W. et al., "Aberrations of the p53 Tumor Suppressor Gene in Human Epithelial Ovarian Carcinoma", Gynecologic Oncology, vol. 57, 1995, pp. 199–204.

Kneppers, L.J. et al., "Point Mutation Screening for 16 Exons of the Dystrophin Gene by Multiplex Single–Strand Conformation Polymorphism Analysis", Human Mutation, vol. 5, 1995, pp. 235–242.

Legagneux, V. et al., "Identification of RNA–binding proteins specific to Xeonpus Eg maternal mRNAs: association with the portion of Eg2 mRNA that promotes deadenylation in embryos", Development, vol. 116, 1992, pp. 1193–1202.

Leng, P. et al., "N–terminal 130 amino acids of MDM2 are sufficient to inhibit p53–mediated transcriptional activation." Oncogene, vol. 10, 1995, pp. 1275–1282.

Levine, A.J. et al., "The 1993 Walter Hubert Lecture: The role of the p53 tumour–suppressor gene in tumorigenesis", Br. J. Cancer, vol. 69, 1994, pp. 409–416.

Li, F. P., "Molecular epidemiology studies of cancer in families", Br. J. Cancer, vol. 68, 1993, pp. 217–219.

McGarvey, T.W. et al., "PCR analysis of exons 4,5 and 6 of the gene p53 in human prostatic adenocarcinoma", Proc. Annu. Meet. Am. Assoc. Cancer Research, vol. 34, 1993, p. 538.

McGoldrick, J. P. et al., "Characterization of a Mammalian Homolog of the *Escherichia coli* MutY Mismatch Repair Protein", Molecular and Cellular Biology, vol. 15, 1995, pp. 989–996.

Milner, B. J. et al., "p53 Mutation is a Common Genetic Event in Ovarian Carcinoma", Cancer Research, vol. 53, 1993, pp. 2128–2138.

Muller, S.J. et al., "Cell Cycle Regulation of a Human Cyclin–like Gene Encoding Uracil–DNA Glycosylase", The Journal of Biological Chemistry, vol. 268, 1993, pp. 1310–1319.

Newburger, P.E. et al., "Mutations in the Promoter Region of the Gene for gp91–phox in X–linked Chronic Granulomatous Disease with Decreased Expression of Cytochrome $b_{558}$ ", J. Clin. Invest., vol. 94, 1994, pp. 1205–1211.

Rajasekaran, A.K. et al., "Functional Characterization of the cis–regulatory elements of the rat ribophorin I gene", Nucleic Acids Research, vol. 23, 1995, pp. 313–319.

Romanczuk, H. et al., "Selective Enhancement of Bovine Papillomavirus Type 1 DNA Replication in *Xenopus laevis* Eggs by the E6 Gene Product", Molecular & Cellular Biology, 1989, pp. 406–414.

SenGupta, D.J. et al., "Strand–Specific Recognition of a Synthetic DNA Replication Fork by the SV40 Large Tumor Antigen", vol. 256, 1992, pp. 1656–1661.

Sharma, A. et al., "Glucose–Induced Transcription of the Insulin Gene is Mediated by Factors Required for ($\beta$–Cell–Type–Specific Expression", Molecular and Cellular Biology, 1994, vol. 14, pp. 871–879.

Shin, T.H. et al., "The transforming growth factor–$\alpha$ gene is a direct target for transcriptional activation by the p53 oncoprotein", Proc. Annu. Meet. Am. Assoc. Cancer Research, vol. 36, 1995, A:259.

Smits, P.H.M. et al., "Regulation of human papillomavirus type 16 (HPV–16) transcription by loci on the short arm of chromosome 11 is mediated by the TATAAAA motif of the HPV–16 promoter", Journal of General Virology, vol. 74, 1993, pp. 121–124.

Sudiro, T.M. et al., "Isolation of Cellular Revertants from a Rat Cell Line Transformed by the E6 and E7 Genes of Human Papillomavirus Type 16", Virology, vol. 182, 1991, pp. 357–360.

Suzuki–Takahashi, I. et al., "The interactions of E2F with pRB and with p107 are regulated via the phosphorylation of pRB and p107 by a cyclin–dependent kinase", Oncogene, vol. 10, 1995 pp. 1691–1698.

Tarunina, M. et al., 6th–p53–Workshop, Nov. 1–5, 1992, Tiberias, Israel, p. 33.

Tjaden, G. et al., "A Novel AT–Rich DNA Binding Protein That Combines an HMG I–like DNA Binding Domain with a Putative Transcription Domain", The Plant Cell, vol. 6, 1994, pp. 107–118.

Unger, T. et al., 6th–p53–Workshop, Nov. 1–5, Tiberias, Israel, p. 33.

Van Ranst, M. et al., "Primary Structure of the E6 Protein of *Micromys minutus* papillomavirus and *Mastomys natalensis* papillomavirus", Nucleic Acids Research, vol. 20, 1992, pp. 2889.

Van Wijnen, A. J. et al., "Transcription of histone H4, H3, and H1 cell cycle genes: Promoter factor HiNF–D contains CDC2, cyclin A, and an RB–related protein", Proc. Natl. Acad. Sci, USA, vol. 91, 1994, pp. 12882–12886.

Von Knebel–Doebertiz, M. et al., "Reversible Repression of Papillomavirus Oncogene Expression in Cervical Carcinomas Cells: Consequences for the Phenotype and E6–p53 and E7–pRB Interactions" Journal of Virology, vol. 68, 1994, pp. 2811–2821.

Wang, X.W. et al., "Hepatitis B virus X protein inhibits p53 sequence–specific DNA binding, transcriptional activity, and association with transcription factor ERCC3." Proc. Natl. Acad. Sci., vol. 91, 1994, pp. 2230–2234.

Weinberg, W.C. et al., "P53 synthesis and p53–mediated transcriptional activation are inversely correlated in proliferating and differentiating mouse keratinocytes", Proc. Annu. Meet. Am. Assoc. Cancer Res., vol. 34, 1993, A:627.

Wu, H., "Analysis of p53 function and regulation", Abstr. Int(B), vol. 55, 1994, p. 1755.

Yew, P.R. et al.,"Adenovirus E1B Oncoprotein tethers a transcriptional repression domain to p53." Genes & Development, vol. 8, 1994, pp. 190–202.

* cited by examiner

ASSAY FOR IDENTIFYING INHIBITORS OF THE INTERACTION BETWEEN PROTEINS P53 AND DM2

This is a continuation of application Ser. No. 09/029,440 filed on Mar. 5, 1998, now abandoned, which is a national phase application under 35 U.S.C. § 371 of PCT/EP96/03957 filed on Sep. 10, 1996, and claims priority under 35 U.S.C. § 119 to European Application No. 95810576.9 filed on Sep. 18, 1995.

The present invention relates to an assay for testing inhibitors of the interaction between proteins p53 and hdm2.

The protein encoded by the human double minute 2 gene, hdm2, forms a complex with the tumor suppressor gene product p53 both in vitro and in vivo. In some human cancers hdm2 is overexpressed and binds most of the cellular p53. Formation of this complex is favoring nucleoplasmic transformation since the complexed p53 looses the tumor suppressor activity. Compounds which prevent the interaction between p53 and hdm2 will release p53, promoting its tumor suppression activity within these cancerous cells. Similar results could also be obtained with animal cancer cells, e. g. in mouse. The mouse homologue to hdm2 is mdm2.

To search for inhibitors of p53-hdm2 interaction, a high throughput primary binding assay, for example ELISA, can be used to select compounds and to initiate a medicinal chemistry program. However, assays which can be used for such a primary screening of p53-hdm2 binding have the disadvantage that artefacts may occur, i. e. wrong positive reaction can be obtained because of artefactual results due to the chemical properties of the tested substances.

In addition, compounds which inhibit the interaction between p53 and hdm2 can also alter p53 specific DNA binding, which is a totally undesired effect because DNA binding is a prerequisite of p53 tumor suppressor activity.

For example, p53 is sensible to several chemical agents that inhibit its activity. The main criteria of activity of p53 is the DNA binding which reveals that the protein is properly folded and not aggregated or unfolded. Compounds which like metal chelators precipitate p53 might be considered as true inhibitors of the p53-hdm2 interaction in a classical binding assay because the precipitated p53 cannot form complexes.

Therefore, additional testing of the impact of the substance on p53-DNA binding is important because compounds inhibiting p53-DNA binding are not good candidates for therapeutic uses. However, in a high through put assay it is not possible to test whether a compound which inhibits p53-hdm2 interaction prevents p53 specific DNA binding or disturbs the p53 conformation so that p53 can no more fulfill the desired biological function.

To avoid these two problems and to start a chemistry program based on more relevant lead compounds, the use of a good confirming assay is crucial.

A confirming assay according to the present invention could, for example, be a gel shift assay. A gel shift of a p53-DNA complex in an agarose gel after incubation with adeno-virus E1B protein is described in Yew et al. [*Genes & Dev.* 8, 190–202, 1994].

In Wang et al. [*PNAS* 91, 2230–2234, 1994] the detection of the binding of HB virus X protein to p53 by measuring the inhibition of p53-DNA binding is described. However, none of the prior art publications describes an assay in which the DNA binding property of p53 remains if p53 is complexed with a double minute 2 protein.

So far, all the in vitro assays described in the literature to study the interaction between p53 and hdm2 are immunoprecipitation assays for testing the binding of hdm2 to p53 [*Leng et al.*, *Oncogene* 10:1275(1995)]. None of these assays simultaneously show that hdm2 binds to p53 and does not disturb its specific DNA binding.

In the present invention it was surprisingly found that p53-DNA binding is maintained after complex formation with hdm2 and that it is possible to measure in one and the same reliable assay the effect of a substance on both the p53-hdm2 and p53-DNA binding.

OBJECT OF THE INVENTION

It is the object of the invention to provide a reliable test method for compounds which inhibit the formation of complexes between hdm2 and p53 but which do not inhibit binding of DNA to p53 or disturb the p53 conformation so that p53 can no more fulfill the desired biological function.

SUMMARY OF THE INVENTION

The present invention concerns a new assay which allows the identification to compounds which inhibit the formation of complexes between a product of the double minute 2 gene ("dm2"), for example human hdm2 or mouse mdm2, and p53 but not between p53 and DNA. Both the complex formation of labeled DNA, C-terminally truncated p53 and dm2 and disruption of dm2 from the labeled DNA-p53 complex by an inhibitor of the p53-dm2 interaction can be detected by a gel shift assay procedure. This assay permits the selection of compounds which, besides their inhibitory property, do not alter p53 specific DNA binding and do not disturb p53 conformation required for DNA binding or formation of active tetramer.

The invention further concerns a test kit for testing the effect of a substance on the binding of a dm2 protein to p53, comprising (a) a p53 or functional equivalent thereof having DNA-binding, oligomerisation and hdm2-binding properties, (b) a hdm2 or functional equivalent thereof having the p53 binding domain, and (c) a DNA sequence specifically binding to the p53 binding domain.

DETAILED DESCRIPTION OF THE INVENTION

The present invention concerns a test method for a substance inhibiting the formation of a complex between p53 and a product of the double minute 2 gene ("dm2"), for example human (h)dm2 or mouse (m)dm2, while not inhibiting the formation of a complex between p53 and DNA. The method comprises measuring complex formation in a mixture of p53, dm2 and DNA binding to p53 in the presence and in the absence of a substance to be tested. In the presence of the desired property of the tested substance, a complex between p53 and DNA is formed ("double complex"), while in the absence of the desired property either a complex between p53, DNA and dm2 ("triple complex"; if no inhibiting activity is present) or no complex (if the tested compound inhibits both the dm2-p53 and p53-DNA complex formation or if the tested substance destroys the p53 conformation so that it is no more DNA binding) is formed. While any method being able to discriminate between the different conditions (triple complex, double complex, no complex) is suitable for performing the present assay, in a preferred embodiment of the invention the assay performed is a gel shift assay.

Thus, the test system essentially comprises a p53, a dm2, and DNA. While the use of the human proteins or active variants thereof is most preferred, the invention is not limited to the use of the human proteins. The corresponding proteins from other species can also be used, e. g. from mouse. However, it is preferred that both the p53 and dm2 protein used in the assay originate from the same species.

For performing the present invention, a p53 protein must be used which both is able to bind DNA and dm2.

p53 according to the present invention can be a recombinant form of p53 or purified from the original organism. It is, however, not necessary to use a full length p53 for performing the present invention. Accordingly, the p53 form used herein also means any useful variant or fragment of p53, preferentially of human p53. The features of such a useful variant or fragment are clear from the description hereinafter.

For DNA binding, p53 must be able to form tetrameric complexes. Consequently, for DNA binding both an active p53 DNA binding domain (e. g. residues 102–292 of p53) and a p53 functional oligomerisation domain (e. g. residues 325–356 of p53) must be present in the p53 form used in the present invention. For improving DNA binding properties of p53, the protein can be activated by interaction with a specific antibody (for example the monoclonal antibody Pab421 known in the art which binds to the amino acid stretch between amino acid 372 and 380 of the human p53), phosphorylation by kinases (casein kinase 11 phosphorylating Ser392 of human p53 or protein kinase C phosphorylating Ser 370 and Ser 375 of human p53) or, more preferably, truncation of its C-terminus (deletion of maximal 38 amino acids of the C-terminus of the natural p53 sequence). An example for the latter is p53D30, i. e. natural p53 lacking the C-terminal 30 amino acids, used in the Examples hereinafter.

In another embodiment of the invention, a p53-DNA complex for studying inhibitors of dm2-p53 interaction can also be obtained by the use of high affinity binding DNA elements (like the RGC and the BC sequences described in Kern et al., Science 252:1708, 1991, and Halazonetis et al., EMBO J 12:1021, 1993, respectively). p53 can be directly purified from various sources (for example from bacteria, baculovirus or mammalian cells).

For being able to form complexes with hdm2, a human p53 suitable for use in the present invention contains residues 1 to 52 of the natural p53 sequence, more preferentially residues: 18 to 23, even more preferentially residues 19, 22 and 23.

The concentration of p53 which is preferentially used in the present invention depends on the amount of dm2 used in the assay. Normally, a five fold excess of dm2 protein is used. A very clear signal in detection of radioactive label is obtained with about 50 to 100 ng of p53D30. However, it is also possible to use higher amounts if it is possible to tolerate in the test assay that some of the proteins precipitate.

A dm2 protein for use in the present invention can be recombinant or purified from the original organism.

A dm2 protein for use in the present invention can be either the full length form or a truncated form or any hybrid protein which contains the minimal p53 binding domain of the dm2. dm2 in context with the present invention means preferentially a dm2 from the same species as the p53 used in the assay is derived from. In particular, if human p53 is used, a human dm2 (hdm2) or analogue thereof containing the minimal p53 binding domain is used, and if mouse p53 is used, a mouse dm2 (mdm2) or analogue thereof containing the minimal p53 binding domain is used. For hdm2, the region from residue 1 to residue 102 of the natural sequence is identified so far as minimal p53 binding domain. For example, in an embodiment of the invention a fusion protein consisting of the N-terminal 188 amino acids of hdm2 (comprising the p53 binding domain) and the full length glutathione S-transferase from *Schistosoma japonicum* prepared in the Examples (named herein G-M fusion protein) can be used for the assay. The fusion protein is obtainable by expressing the DNA encoding the N-terminal 188 amino acids of hdm2 in the expression vector pGEX-2T (Pharmacia).

The DNA element of the test system can be any DNA fragment which specifically binds to p53, e. g. such containing a p53 binding element degenerated or not. It can be a synthetic oligonucleotide, a DNA fragment isolated from living organisms or a DNA element inserted in a plasmid.

The optimal p53 to hdm2 ratio may vary depending on the purity and specific binding activity of the used proteins and, thus, should be determined for each protein variant used.

In the case that a gel shift assay is performed, the DNA element should be such that a DNA band can be detected which shifts in the gel when the DNA is incubated with p53. For detection, the DNA element can be either radiolabeled or possibly labeled by a non radioactive method.

For obtaining a satisfactory detection signal, p53 should be satured with DNA. For example, the $K_D$ of full length p53 activated by antibody Pab421 is about $5 \times 10^{-10}$ M For 50 ng p53D30 used in the Examples, 0.1 to 0.5 pmole of DNA should be sufficient.

For gel shift assay, the gel can be an agarose gel or, preferably, a native polyacrylamide gel, preferably such having 4 to 5% acrylamide. The buffer can be any buffer in which p53 is active for specific DNA binding since the complex p53 -DNA is less stable than the p53 -hdm2 complex. Preferred buffers are HEPES in a concentration of 20 to 50 mM or buffered Tris solution in a concentration of 10to 50 mM.

In a preferred embodiment the pH of the buffer is 7.1 to 8.0. In a preferred embodiment of the invention a salt is present in the buffer. If a salt is used, it should preferentially be KCl at 50 to 100 mM or NaCl at 50 to 175 mM. Moreover, the buffer can optionally contain a substance selected from Glycerol (up to 20%), DTT (up to 0.5 mM), $MgCl_2$ (e. g. about 6 mM), $ZnSO_4$ (e. g. about 0.1. mM), ZnOAc (e. g. about 0.1 mM), detergent NP40 (up to 0.1%), Triton X-100 (up to 0.1%), bovine serum albumin (up to 1 mg/ml), EDTA (up to 1 nM), and a competitor DNA, e. g. poly dl-dc, poly dA-dT or salmon sperm DNA, e. g. in a concentration of 25 to 100 µg/ml.

The invention further concerns a test kit for testing the effect of a substance on the binding of a dm2 protein to p53, said test kit essentially comprising (a) a p53 or functional equivalent thereof having DNA-binding, oligomerisation and hdm2-binding properties, (b) a hdm2 or functional equivalent thereof having the p53 binding domain, and (c) a DNA sequence specifically binding to the p53 binding domain. The preferred ingredients of the test kit are as above. The test kit optionally contains instructions for its use.

The following examples are illustrative, however, should not be construed to limit the present invention.

EXAMPLES

A) Material

Molecular biology reactants are purchased from Promega except the Pfu polymerase which is obtained from Stratagene, the pGEX-2T vector from Pharmacia Biotech and the pET-3a vector from Novagen. Immunologicals are purchased from Oncogene Science. Polydeoxyinosinic-deoxycytidylic acid is obtained from Sigma and [$^{33}$P]$\gamma$-adenosine triphosphate (ATP) from Amersham. The synthetic oligonucleotides are purchased in a purified and desalted form from Microsynth. All other chemicals are from Merck.

B) Molecular Biology

The DNA region of the hdm2 gene encoding the first 188 amino acids of the protein is obtained by Polymerase Chain Reaction (PCR) amplification of the hdm2 gene. The oligonucleotides used for PCR are designed such that a BamHI restriction site is introduced at the 5' extremity of the gene and an EcoRI restriction site at its 3' end (see hdm2 primer I and II with SEQ ID Nos 8 and 9, respectively). The PCR fragments digested by BamHI and EcoRI are ligated with a BamHI/EcoRI cleaved pGEX-2T vector. The resulting vector comprises a fusion gene consisting of the full length sequence of glutathione-S-transferase of *S. japonicum*, a linker sequence, and the N-terminal 188 amino acids of hdm2, in the 5' to 3' order. The complete gene is sequenced on both strands and the recombinant plasmid is introduced into *E. coli* strain BL21 (Novagen).

Glutathione-S-transferase protein (for control experiments) was obtained from *E. coli* strain BL21 (Novagen) transformed with pGEX-2T plasmid.

The human wild type p53 gene is used as a template for PCR to obtain the gene fragment encoding for residues 1 to 362 of the 392 amino acids of natural p53 (p53D30). The oligonucleotides used for PCR are designed such that a NdeI restriction site is introduced at the 5' end and a BamHI site at the 3' end (see p53D30 primer I and II with SEQ ID Nos 10 and 11, respectively).

The PCR fragments digested by NdeI and BamHI are ligated with a NdeI/BamHI cleaved pET-3a plasmid. The complete gene is sequenced and the expression plasmid is introduced into *E. coli* strain BL21(DE3)pLysS (Novagen).

C) Protein Expression

For protein expression bacteria cultures are inoculated by a 100-fold diluted overnight culture and grown in Luria Broth medium in the presence of 100 $\mu$g ampicillin/ml at 37° C. to $OD_{600}$=0.8. The cultures are then cooled on ice to room temperature, induced with 1 mM isopropyl-D-thiogalactopyranoside and grown for four additional hours at 27° C. The cells are then harvested by centrifugation and the pellets flash frozen in liquid nitrogen and stored at −70° C.

D) Purification of the hdm2 Fusion Protein and of the Glutathione S-transferase Protein The cell pellets containing the glutathione S-transferase fusion protein of hdm2 (named "G-M" in the following) are resuspended in ice cold buffer A (0.5 M NaCI, 2.7 mM KCI, 10 mM $Na_2HPO_4$, 1.8 mM $KH_2PO_4$, 1 mM ethylenediaminetetraacetic acid (EDTA), 10 mM 2-mercaptoethanol, 1 mM phenylmethanesulfonylfluoride (PMSF)-pH=7.3) and lysed with a French press at 1000 psi. After centrifugation, the soluble fraction is loaded onto a Glutathione Sepharose 4B column (Pharmacia Biotech) preequilibrated at 4° C. with buffer A. The G-M fusion protein is then eluted with buffer B (50 mM Tris(hydroxymethyl)-aminomethane (Tris-HCI), 10 mM reduced glutathione, 0.5 M NaCI, 1 mM EDTA, 1 mM PMSF, 10 mM 2-mercaptoethanol-pH=8.0). The fractions containing the protein are identified by SDS-PAGE (sodium dodecyl sulfate polyacryalmide gel electrophoresis), pooled and desalted on a Sephadex G25 column (Pharmacia Biotech) which is preequilibrated at 4° C. with buffer C (50 mM Tris. HCI, 50 mM NaCI, 20% (v/v) glycerol, 10 mM 2-mercaptoethanol, 0.1% (v/v) Triton X-100 –pH=7.6). The protein solution is loaded onto a Mono Q column (Pharmacia Biotech), preequilibrated with buffer C at 4° C., and the fusion protein eluted with a linear gradient of buffer C containing 1 M NaCI. The fractions containing the purified G-M protein are pooled, concentrated (Centricon 30—Amicon) to 1 mg/ml, flash frozen in liquid nitrogen and stored at −70° C.

The glutathione S-transferase protein (named "G" in the following) is purified in the same procedure except that the purification is stopped after the Glutathione Sepharose 4B column due to the high purity of the material obtained after this step.

E) Purification of p53D30 Protein

The cell pellets containing the p53D30 protein are resuspended in ice cold buffer D (50 mM 4-(2-hydroxyethyl)-piperazine-ethane-sulfonic acid (Hepes. NaOH), 10% (v/v) glycerol, 0.1 mM EDTA, 0.1% (v/v) Triton X-100,5 mM 1,4-dithio-DL-threitol (DTT), 1 mM PMSF–pH=7.6) and lysed with a French press at 1000 psi. After centrifugation, the soluble fraction is loaded onto a HiTrap Heparin column (Pharmacia Biotech) preequilibrated at 4° C. with buffer D. The column is first washed with buffer D containing 22% buffer E (50 mM Hepes. NaOH, 1 M KCI, 10% (v/v) glycerol–pH=7.6) and p53D30 is eluted with a linear gradient to 100% buffer E. The fractions containing p53D30 are pooled and loaded onto a HiTrap metal chelation column (Pharmacia Biotech) charged with nickel and preequilibrated at 4° C. with buffer F (50 mM Hepes. NaOH, 0.5 M KCI, 10% (v/v) glycerol–pH =7. 6). After washing the column with buffer F containing 20% buffer G (50 mM Hepes. NaOH, 0.5 M KCI, 10% (v/v) glycerol, 0.1 M immidazole–pH=7.6), p53D30 is eluted with 45% buffer G. 50 mM 2-mercaptoethanol and 1 mM ZnCI2 are added to the solution and the protein is dialysed at 4 ° C against 50 mM Hepes. NaOH, 0.5 M KCI, 20% (v/v) glycerol, 50 mM 2-mercaptoethanol, 1 mM ZnCI2–pH=7.6. p53D30 is concentrated to 1 mg/ml (Amicon 30 kDa cut off membrane), flash frozen in liquid nitrogen and stored at −70° C.

F) Protein Analysis

The purity of the protein preparation is evaluated by gel scanning (Schimadzu CS-930) on a SDS-PAGE (Laemmli, U.K. (1970) Nature, 227, 680-385) stained with Coomassie blue. Protein concentration is determined according to Bradford, M. B. (1976) Anal. Biochem., 72, 248-254).

G) Peptide Synthesis

Peptide A (Ac-SQETFSDLWKL) shown in SEQ ID No. 5 is assembled on a Milligen 9050 automated peptide synthesizer (continuos flow) by solid—phase peptide synthesis using the fluorenylmethoxycarbonyl (Fmoc) strategy on Fmoc-MBHA-PAL-PEG amid resin. Side-chain protection of a-Fmoc amino acids is as follows: Asp(O-tertiobutyloxycarbonyl), Gln(Trt), Glu(O-tertiobutyloxycarbonyl), Lys (butyloxycarbonyo, Ser (tertiobutyl), Trp(butyloxycarbonyl), Thr(tertiobutyl). The a-Fmoc amino acids (3 equivalents) are incorporated using the respective trichlorophenyl esters. Each coupling step is followed by an end—capping step ($Ac_2O$/pyridine in dimethyl formamide). After completion of the chain assembly, the dried peptide resin is treated with 76% (v/v) trifluroacetic acid (TFA)/20% (v/v) EDT/4% (v/v) water at 30° C. in order to cleave the peptide from the resin and to deblock the side—chain protection. After 3 h incubation, the resin is separated by filtration and the peptide precipitated in cold (0° C.) tert-butyl-methyl ether. The crude peptide is collected by centrifugation and purified by preparative reversed-phase medium-pressure liquid chromatography using a Vydac $C_{18}$ column (acetonitrile—water gradient containing 0.1% (v/v) TFA) to yield the final product. The purity and the correct mass of the peptide is verified by analytical reversed—phase high pressure liquid chromatography, FABMS and matrix—assisted laser desorption ionisation time—of—flight mass spectrometry.

To the determine Peptide A concentration in solution, the peptide is dissolved in 50 mM Tris.HCI–pH=7.6 and incubated for 10 min at 37° C. The solution is extensively mixed and incubated for 15 min on ice. The insoluble fraction is eliminated by centrifugation at 13000 rpm for 10 min and the peptide concentration is determined by spectrophotometry at 280 nm using a molecular extinction coefficient of 5690.

H) Gel Shift Assay

Oligonucleotides I and II (SEQ ID Nos. 6 and 7, respectively) containing the 20-mer p53 consensus DNA binding site and HindIII-compatible ends are hybridised and 5' end-labelled with [$^{33}$P]γ-ATP as described in Maniatis, T. , Fritsch, E. F. and Sambrook, J. (1989) Molecular Cloning, A Laboratory Manual, Cold Spring Harbor Laboratory, New York.

A 20 μl reaction volume containing 50 mM Tris. HCI, 50 mM NaCI, 5% (v/v) glycerol, 0.1% (v/v) Triton X-100, 10 mM DTT and 50 μg/ml polydeoxyinosinic-deoxycytidylic acid–pH=7.6 (binding buffer) are incubated for 30 min at 22° C. in the presence of the indicated amounts of p53D30, of radiolabelled oligonucleotides and of the mentioned monoclonal antibodies. Reactions are loaded onto a native 4% polyacrylamide gel containing 0.5×Tris.HCI–boric acid–pH=8.0 which had undergone pre-electrophoresis at 200 V for 45 min at 4 ° C. Electrophoresis is continued at 200 V from 90 to 120 min at 4° C. Gels are dried prior exposure to X-ray film (Amersham Hyperfilm-MP).

To perform the p53D30-G-M-DNA ternary complex both proteins and the radiolabeled DNA are incubated in binding buffer for 30 min at 22° C. and the gel is proceeded as described previously.

What is claimed is:

1. A method for identifying a substance that inhibits the binding of a dm2 protein to p53, while does not inhibit binding of p53 to DNA, the method comprising the steps of:
   (1) combining (a) a first protein which comprises a p53 DNA-binding domain and a p53 oligomerisation domain and wnich is able to bind to drm2, (b) a second protein which comprises a p53 binding domain from dm2, (c) a DNA fragment comprising a p53 binding domain, and (d) the substance to be tested;
   (2) discriminating between (i) the formation of a double complex of the first protein and the DNA fragment, which indicates that the substance has the ability to inhibit binding of a dm2 protein to p53, while not inhibiting binding of p53 to DNA, (ii) the formation of a triple complex of the first protein, the second protein and the DNA fragment, which indicates that the substance does not have the ability to inhibit binding of a dm2 protein to p53, and (iii) the non-formation of a complex between the first protein and the DNA fragment, which indicates that the substance inhibits the binding of p53 to DNA; and
   (3) identifying a substance which allows the formation of the double complex of (i).

2. The method according to claim 1 characterized in that complex formation is tested by gel shift assay.

3. The method according to claim 1 characterized in that human p53 is used.

4. The method according to claim 1 characterized in that the p53 used is p53D30.

5. The method according to claim 1 characterized in that hdm2 is used.

6. The method according to claim 1 wherein the second protein is a truncated dm2 with p53 binding properties.

7. The method according to claim 1 wherein the second protein comprises the N-terminal 188 amino acids of hdm2.

8. The method according to claim 1 wherein the second protein is a fusion protein comprising glutathion-S-transferase of *S. japonicum* and the N-terminal 188 amino acids of hdm2.

9. The method of claim 1 in which both the binding of hdm2 to p53 and the binding of p53 to DNA is tested at the same time.

* * * * *

UNITED STATES PATENT AND TRADEMARK OFFICE
CERTIFICATE OF CORRECTION

PATENT NO. : 6,492,116 B1
DATED : December 10, 2002
INVENTOR(S) : Chene et al.

It is certified that error appears in the above-identified patent and that said Letters Patent is hereby corrected as shown below:

Column 17,
Line 35, should read -- domain and which is able... --

Signed and Sealed this

Eighteenth Day of November, 2003

JAMES E. ROGAN
*Director of the United States Patent and Trademark Office*

SEQUENCE LISTING

```
<160> NUMBER OF SEQ ID NOS: 11

<210> SEQ ID NO 1
<211> LENGTH: 1098
<212> TYPE: DNA
<213> ORGANISM: Homo sapiens
<220> FEATURE:
<221> NAME/KEY: CDS
<222> LOCATION: (4)..(1092)
<223> OTHER INFORMATION: Residue 1 to 362 of human p53 protein (named
      p53D30)

<400> SEQUENCE: 1 cat atg gag gag ccg cag tca gat cct agc gtc gag ccc cct ctg agt        48
    Met Glu Glu Pro Gln Ser Asp Pro Ser Val Glu Pro Pro Leu Ser
    1               5                   10                  15 cag gaa aca ttt tca gac cta tgg aaa cta ctt cct gaa aac aac gtt        96
Gln Glu Thr Phe Ser Asp Leu Trp Lys Leu Leu Pro Glu Asn Asn Val
                20                  25                  30 ctg tcc ccc ttg ccg tcc caa gca atg gat gat ttg atg ctg tcc ccg       144
Leu Ser Pro Leu Pro Ser Gln Ala Met Asp Asp Leu Met Leu Ser Pro
            35                  40                  45 gac gat att gaa caa tgg ttc act gaa gac cca ggt cca gat gaa gct       192
Asp Asp Ile Glu Gln Trp Phe Thr Glu Asp Pro Gly Pro Asp Glu Ala
        50                  55                  60 ccc aga atg cca gag gct gct ccc ccc gtg gcc cct gca cca gca gct       240
Pro Arg Met Pro Glu Ala Ala Pro Pro Val Ala Pro Ala Pro Ala Ala
    65                  70                  75 cct aca ccg gcg gcc cct gca cca gcc ccc tcc tgg ccc ctg tca tct       288
Pro Thr Pro Ala Ala Pro Ala Pro Ala Pro Ser Trp Pro Leu Ser Ser
80                  85                  90                  95 tct gtc cct tcc cag aaa acc tac cag ggc agc tac ggt ttc cgt ctg       336
Ser Val Pro Ser Gln Lys Thr Tyr Gln Gly Ser Tyr Gly Phe Arg Leu
                100                 105                 110 ggc ttc ttg cat tct ggg aca gcc aag tct gtg act tgc acg tac tcc       384
Gly Phe Leu His Ser Gly Thr Ala Lys Ser Val Thr Cys Thr Tyr Ser
            115                 120                 125 cct gcc ctc aac aag atg ttt tgc caa ctg gcc aag acc tgc cct gtg       432
Pro Ala Leu Asn Lys Met Phe Cys Gln Leu Ala Lys Thr Cys Pro Val
        130                 135                 140 cag ctg tgg gtt gat tcc aca ccc ccg ccc ggc acc cgc gtc cgc gcc       480
```

-continued

```
               Gln Leu Trp Val Asp Ser Thr Pro Pro Gly Thr Arg Val Arg Ala
                   145                 150                 155 atg gcc atc tac aag cag tca cag cac atg acg gag gtt gtg agg cgc      528
Met Ala Ile Tyr Lys Gln Ser Gln His Met Thr Glu Val Val Arg Arg
160                 165                 170                 175 tgc ccc cac cat gag cgc tgc tca gat agc gat ggt ctg gcc cct cct      576
Cys Pro His His Glu Arg Cys Ser Asp Ser Asp Gly Leu Ala Pro Pro
                180                 185                 190 cag cat ctt atc cga gtg gaa gga aat ttg cgt gtg gag tat ttg gat      624
Gln His Leu Ile Arg Val Glu Gly Asn Leu Arg Val Glu Tyr Leu Asp
            195                 200                 205 gac aga aac act ttt cga cat agt gtg gtg gtg ccc tat gag ccg cct      672
Asp Arg Asn Thr Phe Arg His Ser Val Val Val Pro Tyr Glu Pro Pro
        210                 215                 220 gag gtt ggc tct gac tgt acc acc atc cac tac aac tac atg tgt aac      720
Glu Val Gly Ser Asp Cys Thr Thr Ile His Tyr Asn Tyr Met Cys Asn
    225                 230                 235 agt tcc tgc atg ggc ggc atg aac cgg agg ccc atc ctc acc atc atc      768
Ser Ser Cys Met Gly Gly Met Asn Arg Arg Pro Ile Leu Thr Ile Ile
240                 245                 250                 255 aca ctg gaa gac tcc agt ggt aat cta ctg gga cgg aac agc ttt gag      816
Thr Leu Glu Asp Ser Ser Gly Asn Leu Leu Gly Arg Asn Ser Phe Glu
                260                 265                 270 gtg cgt gtt tgt gcc tgt cct ggg aga gac cgg gcc aca gag gaa gag      864
Val Arg Val Cys Ala Cys Pro Gly Arg Asp Arg Ala Thr Glu Glu Glu
            275                 280                 285 aat ctc cgc aag aaa ggg gag cct cac cac gag ctg ccc cca ggg agc      912
Asn Leu Arg Lys Lys Gly Glu Pro His His Glu Leu Pro Pro Gly Ser
        290                 295                 300 act aag cga gca ctg ccc aac aac acc agc tcc tct ccc cag cca aag      960
Thr Lys Arg Ala Leu Pro Asn Asn Thr Ser Ser Ser Pro Gln Pro Lys
    305                 310                 315 aag aaa cca ctg gat gga gaa tat ttc acc ctt cag atc cgt ggg cgt     1008
Lys Lys Pro Leu Asp Gly Glu Tyr Phe Thr Leu Gln Ile Arg Gly Arg
320                 325                 330                 335 gag cgc ttc gag atg ttc cga gag ctg aat gag gcc ttg gaa ctc aag     1056
Glu Arg Phe Glu Met Phe Arg Glu Leu Asn Glu Ala Leu Glu Leu Lys
                340                 345                 350 gat gcc cag gct ggg aag gag cca ggg ggg agc tga ggatcc              1098
Asp Ala Gln Ala Gly Lys Glu Pro Gly Gly Ser
            355                 360

<210> SEQ ID NO 2
<211> LENGTH: 362
<212> TYPE: PRT
<213> ORGANISM: Homo sapiens

<400> SEQUENCE: 2

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
```

-continued

```
                   85                  90                  95
Val Pro Ser Gln Lys Thr Tyr Gln Gly Ser Tyr Gly Phe Arg Leu Gly
            100                 105                 110
Phe Leu His Ser Gly Thr Ala Lys Ser Val Thr Cys Thr Tyr Ser Pro
        115                 120                 125
Ala Leu Asn Lys Met Phe Cys Gln Leu Ala Lys Thr Cys Pro Val Gln
    130                 135                 140
Leu Trp Val Asp Ser Thr Pro Pro Gly Thr Arg Val Arg Ala Met
145                 150                 155                 160
Ala Ile Tyr Lys Gln Ser Gln His Met Thr Glu Val Val Arg Arg Cys
            165                 170                 175
Pro His His Glu Arg Cys Ser Asp Ser Asp Gly Leu Ala Pro Pro Gln
        180                 185                 190
His Leu Ile Arg Val Glu Gly Asn Leu Arg Val Glu Tyr Leu Asp Asp
    195                 200                 205
Arg Asn Thr Phe Arg His Ser Val Val Pro Tyr Glu Pro Pro Glu
    210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
            245                 250                 255
Leu Glu Asp Ser Ser Gly Asn Leu Leu Gly Arg Asn Ser Phe Glu Val
        260                 265                 270
Arg Val Cys Ala Cys Pro Gly Arg Asp Arg Arg Thr Glu Glu Asn
    275                 280                 285
Leu Arg Lys Lys Gly Glu Pro His His Glu Leu Pro Pro Gly Ser Thr
    290                 295                 300
Lys Arg Ala Leu Pro Asn Asn Thr Ser Ser Ser Pro Gln Pro Lys Lys
305                 310                 315                 320
Lys Pro Leu Asp Gly Glu Tyr Phe Thr Leu Gln Ile Arg Gly Arg Glu
            325                 330                 335
Arg Phe Glu Met Phe Arg Glu Leu Asn Glu Ala Leu Glu Leu Lys Asp
        340                 345                 350
Ala Gln Ala Gly Lys Glu Pro Gly Gly Ser
    355                 360
```

<210> SEQ ID NO 3
<211> LENGTH: 729
<212> TYPE: DNA
<213> ORGANISM: Homo sapiens
<220> FEATURE:
<221> NAME/KEY: CDS
<222> LOCATION: (84)..(650)
<223> OTHER INFORMATION: N-terminal 188 amino acids of human double
      minute protein 2

<400> SEQUENCE: 3

```
tagcatggcc tttgcagggc tggcaagcca cgtttggtgg tggcgaccat cctccaaaat      60
cggatctggt tccgcgtgga tcc atg tgc aat acc aac atg tct gta cct act     113
                         Met Cys Asn Thr Asn Met Ser Val Pro Thr
                          1               5                  10 gat ggt gct gta acc acc tca cag att cca gct tcg gaa caa gag acc       161
Asp Gly Ala Val Thr Thr Ser Gln Ile Pro Ala Ser Glu Gln Glu Thr
                15                  20                  25 ctg gtt aga cca aag cca ttg ctt ttg aag tta tta aag tct gtt ggt       209
Leu Val Arg Pro Lys Pro Leu Leu Leu Lys Leu Leu Lys Ser Val Gly
        30                  35                  40
```

-continued

```
gca caa aaa gac act tat act atg aaa gag gtt ctt ttt tat ctt ggc    257
Ala Gln Lys Asp Thr Tyr Thr Met Lys Glu Val Leu Phe Tyr Leu Gly
         45                  50                  55 cag tat att atg act aaa cga tta tat gat gag aag caa caa cat att    305
Gln Tyr Ile Met Thr Lys Arg Leu Tyr Asp Glu Lys Gln Gln His Ile
 60                  65                  70 gta tat tgt tca aat gat ctt cta gga gat ttg ttt ggc gtg cca agc    353
Val Tyr Cys Ser Asn Asp Leu Leu Gly Asp Leu Phe Gly Val Pro Ser
 75                  80                  85                  90 ttc tct gtg aaa gag cac agg aaa ata tat acc atg atc tac agg aac    401
Phe Ser Val Lys Glu His Arg Lys Ile Tyr Thr Met Ile Tyr Arg Asn
                 95                 100                 105 ttg gta gta gtc aat cag cag gaa tca tcg gac tca ggt aca tct gtg    449
Leu Val Val Val Asn Gln Gln Glu Ser Ser Asp Ser Gly Thr Ser Val
                110                 115                 120 agt gag aac agg tgt cac ctt gaa ggt ggg agt gat caa aag gac ctt    497
Ser Glu Asn Arg Cys His Leu Glu Gly Gly Ser Asp Gln Lys Asp Leu
            125                 130                 135 gta caa gag ctt cag gaa gag aaa cct tca tct tca cat ttg gtt tct    545
Val Gln Glu Leu Gln Glu Glu Lys Pro Ser Ser Ser His Leu Val Ser
        140                 145                 150 aga cca tct acc tca tct aga agg aga gca att agt gag aca gaa gaa    593
Arg Pro Ser Thr Ser Ser Arg Arg Arg Ala Ile Ser Glu Thr Glu Glu
155                 160                 165                 170 aat tca gat gaa tta tct ggt gaa cga caa aga aaa cgc cac aaa tct    641
Asn Ser Asp Glu Leu Ser Gly Glu Arg Gln Arg Lys Arg His Lys Ser
                175                 180                 185 gat agt tga  gaattcatcg tgactgactg acgatctgcc tcgcgcgttt           690
Asp Ser
cggtgatgac ggtgaaaacc tctgacacat gcagctccc                         729
```

<210> SEQ ID NO 4
<211> LENGTH: 188
<212> TYPE: PRT
<213> ORGANISM: Homo sapiens

<400> SEQUENCE: 4

```
Met Cys Asn Thr Asn Met Ser Val Pro Thr Asp Gly Ala Val Thr Thr
 1               5                  10                  15

Ser Gln Ile Pro Ala Ser Glu Gln Glu Thr Leu Val Arg Pro Lys Pro
                 20                  25                  30

Leu Leu Leu Lys Leu Leu Lys Ser Val Gly Ala Gln Lys Asp Thr Tyr
             35                  40                  45

Thr Met Lys Glu Val Leu Phe Tyr Leu Gly Gln Tyr Ile Met Thr Lys
 50                  55                  60

Arg Leu Tyr Asp Glu Lys Gln Gln His Ile Val Tyr Cys Ser Asn Asp
 65                  70                  75                  80

Leu Leu Gly Asp Leu Phe Gly Val Pro Ser Phe Ser Val Lys Glu His
                 85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160
```

```
Arg Arg Arg Ala Ile Ser Glu Thr Glu Asn Ser Asp Glu Leu Ser
            165                 170                 175
Gly Glu Arg Gln Arg Lys Arg His Lys Ser Asp Ser
            180                 185

<210> SEQ ID NO 5
<211> LENGTH: 11
<212> TYPE: PRT
<213> ORGANISM: Artificial Sequence
<220> FEATURE:
<221> NAME/KEY: SITE
<222> LOCATION: (1)
<223> OTHER INFORMATION: N-acetyl serine in position 1
<223> OTHER INFORMATION: Description of Artificial Sequence: Synthetic

<400> SEQUENCE: 5

Ser Gln Glu Thr Phe Ser Asp Leu Trp Lys Leu
 1               5                  10

<210> SEQ ID NO 6
<211> LENGTH: 26
<212> TYPE: DNA
<213> ORGANISM: Artificial Sequence
<220> FEATURE:
<221> NAME/KEY: protein_bind
<222> LOCATION: (5)..(26)
<223> OTHER INFORMATION: p53 consensus binding site
<223> OTHER INFORMATION: Description of Artificial Sequence:
      Oligonucleotide

<400> SEQUENCE: 6
agcttagaca tgcctagaca tgccta                                        26

<210> SEQ ID NO 7
<211> LENGTH: 26
<212> TYPE: DNA
<213> ORGANISM: Artificial Sequence
<220> FEATURE:
<221> NAME/KEY: protein_bind
<222> LOCATION: (5)..(26)
<223> OTHER INFORMATION: p53 consensus binding site
<223> OTHER INFORMATION: Description of Artificial Sequence:
      Oligonucleotide

<400> SEQUENCE: 7
agcttaggca tgtctaggca tgtcta                                        26

<210> SEQ ID NO 8
<211> LENGTH: 34
<212> TYPE: DNA
<213> ORGANISM: Artificial Sequence
<220> FEATURE:
<223> OTHER INFORMATION: PCR primer for cloning hdm2 N-terminal 188
      aminoacid coding
<223> OTHER INFORMATION: Description of Artificial Sequence: Primer

<400> SEQUENCE: 8
gatccgggat ccatgtgcaa taccaacatg tctg                               34

<210> SEQ ID NO 9
<211> LENGTH: 38
<212> TYPE: DNA
<213> ORGANISM: Artificial Sequence
<220> FEATURE:
<223> OTHER INFORMATION: PCR primer for cloning hdm2 N-terminal 188
      aminoacid coding
<223> OTHER INFORMATION: Description of Artificial Sequence: Primer

<400> SEQUENCE: 9
```

-continued

```
gatccggaat tctcaactat cagatttgtg gcgttttc                    38

<210> SEQ ID NO 10
<211> LENGTH: 31
<212> TYPE: DNA
<213> ORGANISM: Artificial Sequence
<220> FEATURE:
<223> OTHER INFORMATION: PCR primer for p53D30 cloning
<223> OTHER INFORMATION: Description of Artificial Sequence: Primer

<400> SEQUENCE: 10
gatccgcata tggaggagcc gcagtcagat c                           31

<210> SEQ ID NO 11
<211> LENGTH: 36
<212> TYPE: DNA
<213> ORGANISM: Artificial Sequence
<220> FEATURE:
<223> OTHER INFORMATION: PCR primer for p53D30 cloning
<223> OTHER INFORMATION: Description of Artificial Sequence: Primer

<400> SEQUENCE: 11
gatccgggat cctcagctcc ccctggctc cttccc                       36
```